United States Patent
Wefer et al.

(10) Patent No.: US 12,195,422 B2
(45) Date of Patent: Jan. 14, 2025

(54) PROCESS FOR THE PREPARATION OF D,L-METHIONINE

(71) Applicant: Evonik Operations GmbH, Essen (DE)

(72) Inventors: Johannes Wefer, Singapore (SG); Hans-Joachim Hasselbach, Gelnhausen (DE); Tobias Winkler, Hanau (DE); Danny De Corte, Sint-Niklaas (BE); Bernd Drapal, Alzenau (DE); Imad Moussallem, Hanau (DE); Christian Renner, Gruendau (DE); Christian Rückriegel, Biebergemuend (DE)

(73) Assignee: Evonik Operations GmbH, Essen (DE)

( * ) Notice: Subject to any disclaimer, the term of this patent is extended or adjusted under 35 U.S.C. 154(b) by 616 days.

(21) Appl. No.: 17/619,911

(22) PCT Filed: Jun. 17, 2020

(86) PCT No.: PCT/EP2020/066761
§ 371 (c)(1),
(2) Date: Dec. 16, 2021

(87) PCT Pub. No.: WO2020/254403
PCT Pub. Date: Dec. 24, 2020

(65) Prior Publication Data
US 2022/0306574 A1    Sep. 29, 2022

(30) Foreign Application Priority Data

Jun. 18, 2019 (EP) .................................. 19180892

(51) Int. Cl.
C07C 319/20 (2006.01)
C07C 319/28 (2006.01)
C07C 323/58 (2006.01)

(52) U.S. Cl.
CPC .......... *C07C 319/20* (2013.01); *C07C 319/28* (2013.01); *C07C 323/58* (2013.01); *C07B 2200/13* (2013.01)

(58) Field of Classification Search
CPC .... C07C 319/20; C07C 319/28; C07C 323/58
See application file for complete search history.

(56) References Cited

U.S. PATENT DOCUMENTS 2,717,252 A * 9/1955 Holland ............... C07D 233/78
562/559
5,770,769 A * 6/1998 Geiger ................. C07D 233/76
562/559

(Continued)

FOREIGN PATENT DOCUMENTS

JP    4482973 B2 *  6/2010  ........... C07C 319/20

OTHER PUBLICATIONS

International Search Report and Written Opinion issued on Aug. 25, 2020 in PCT/EP2020/066761 filed Jun. 17, 2020, 10 pages.

(Continued)

*Primary Examiner* — Yate' K Cutliff
(74) *Attorney, Agent, or Firm* — Oblon, McClelland, Maier & Neustadt, L.L.P.

(57) ABSTRACT

The invention relates to a single cycle process for preparing D,L-methionine from an alkali methioninate solution obtained by alkaline hydrolysis of 5-(2-methylmercaptoethyl)hydantoin, in which the D,L-methionine is obtained by neutralizing the alkali methioninate solution with carbon dioxide at elevated temperature and subsequently crystallizing D,L-methionine in the presence of seed crystals.

14 Claims, 11 Drawing Sheets

(56) References Cited

U.S. PATENT DOCUMENTS

| | | | |
|---|---|---|---|
| 5,990,349 A | 11/1999 | Geiger et al. | |
| 2015/0051421 A1* | 2/2015 | Koerfer | C07C 319/28 562/550 |
| 2016/0068480 A1 | 3/2016 | Koerfer et al. | |

OTHER PUBLICATIONS

Extended European Search Report issued on Dec. 19, 2019 in European Patent Application No. 19180892.2 filed Jun. 18, 2019, 6 pages.

* cited by examiner

PROCESS FOR THE PREPARATION OF D,L-METHIONINE

FIELD OF THE INVENTION

The present invention relates to a simplified process for the preparation of D,L-methionine, which allows crystallization from highly concentrated process solution.

BACKGROUND OF THE INVENTION

The amino acid methionine is currently industrially produced worldwide in large amounts and is of considerable commercial importance. Methionine is employed in many fields, such as pharmaceutical, health and fitness products, but particularly as additive in many feedstuffs for various livestock.

On an industrial scale, D,L-methionine (in the following: methionine) is produced chemically via the Bucherer-Bergs reaction, which is a variant of the Strecker synthesis. Here, the starting substances 3-methylmercaptopropanal (prepared from 2-propenal and methyl mercaptan), hydrocyanic acid (hydrogen cyanide, HCN), ammonia and carbon dioxide are reacted to give 5-(2-methylmercaptoethyl)hydantoin ("methionine hydantoin"), which is hydrolysed to methioninate and finally neutralized to liberate methionine. There are several process variants for hydrolysis and neutralization described. This invention is particularly suitable for the potassium carbonate process, in which hydrolysis is accomplished with potassium carbonate and potassium hydrogen carbonate to give potassium methioninate and subsequent liberation of methionine from its potassium salt by treatment with carbon dioxide ("carbonation reaction"). The methionine product is filtered off as a precipitate from the mother liquor containing potassium hydrogen carbonate (U.S. Pat. No. 5,770,769). Methionine precipitates out of the process solution in form of very flat leaflets, which are difficult to handle and slowly separate from the mother liquor (EP1451139 B).

In order to obtain the methionine product in sufficient purity and quality, the raw methionine usually has to be dissolved and recrystallized from an aqueous solution, filtered off and finally dried. The recrystallization is preferably carried out as a two stage vacuum crystallization with different temperature levels (EP1451139 B).

There have been developed different strategies to improve crystallization and filtration.

CN 206642401 U describes an alternative recrystallization technology, in which a crystallization unit is characterized, that allows cooling crystallization via direct heat exchanger within the stirred crystallizer. Further, the presence of crystallization additives in the recrystallization step are used to improve filtration properties and bulk density of methionine. JP 2004292324 A claims polyvinyl alcohol or gluten as crystallization additives, EP2641898 A1 employs ionic and non-ionic surfactants (e.g. linear, branched or cyclic alkyl, alkenyl or arylsulfates) and EP 1451139 B1 applies hydroxyethyl cellulose or hydroxymethyl cellulose to increase bulk density. Variants of the potassium carbonate process in which the methionine product is obtained directly from the process matrix without recrystallization are described in the literature.

JP 4482973 B and JPH04169570 describe the carbonation with the help of crystallization additives at 15-30° C. Herein, carbon dioxide is added to the liquid phase neutralization (carbonation) and the methionine precipitates (13 wt. % methionine). However, agglomeration to larger particles occurs in the presence of high concentrations of organic flocculants, such as caseine, polyvinyl alcohol or hydroxypropyl methylcellulose (up to 3000 ppm required). Obtained spherical agglomerated particles are characterized by improved filtration properties and low moisture content.

To increase bulk density, CN1178909 describes a two stage carbonation process in which seed crystals are generated in a batch crystallization, in which above used flocculants are present, and those were fed in a second semi continuous crystallization step where potassium methioninate (13.3 wt. % methionine, initial concentration) is carbonized in the presence of previously generated agglomerated particles.

CN 104744326 B pertains to neutralization crystallization in a Draft-Tube-Baffel crystallizer. Carbonation and crystallization are conducted in a continuous reactor at 20-30° C. Cooled potassium methioninate solution (15 wt. % methionine) is sprayed into a carbon dioxide atmosphere in the upper part of the reactor and the neutralized solution begins to crystallize. The newly formed crystals descend with the mother liquor into the lower part of the crystallizer and can grow further. Larger crystals are separated off. Smaller crystals are dissolved again, mixed with the potassium methioninate solution and recycled. This process provides agglomerated products in high bulk density.

Further, two variants of alternative processes (sodium sulfate methionine process, biotechnological process of L-methionine) apply the following crystallization technologies to improve the quality of the crystalline methionine. The described process matrix for both processes is different in comparison to the potassium carbonate process.

CN 108794363 A relates to a method for crystallization of methionine from sodium sulfate process solution (8 wt. % methionine, initial concentration). The process solution is neutralized with sulfuric acid and cooled with defined cooling rates in the presence of seed crystals to obtain crystalline methionine with a high bulk density.

KR 20180078621 A describes a method for production of high bulk density crystalline L-methionine using crystallization techniques. The manufacturing method includes pH adjustment via different reagents (specifically pH 2.0-3.0 or pH 8.0-9.0), complete dissolution by heating and finally temperature controlled crystallization by various type of cooling (graduation, evaporation, freezing etc.). The initial concentration of methionine in given examples does not exceed 13 wt. %.

In view of the above, it is the objective of the present invention to provide a simplified and highly concentrated process for the continuous, semi-continuous or batch-wise preparation of methionine. The process can be used to obtain a readily filterable crystalline methionine product, having a high bulk density of up to 600 g/L and purity of >99% methionine content. This objective is solved by the process according to the present invention as described below.

SUMMARY OF THE INVENTION

The present invention provides a process for the preparation of D,L-methionine in which an alkali methioninate solution is obtained by alkaline hydrolysis of 5-(2-methylmercaptoethyl)hydantoin, the process comprising the consecutive steps of (a) neutralizing the alkali methioninate solution at a temperature of between 65° C. and 95° C. by turbulent mixing with carbon dioxide in order to obtain a neutralized process solution and (b) crystallizing the D,L-methionine product in the presence of D,L-methionine seed crystals by cooling the process solution to a temperature range of between 25° C. and 35° C.

DETAILED DESCRIPTION OF THE INVENTION

The inventors have unexpectedly found that the above-described methionine process including the alkaline hydrolysis of methionine hydantoin can be conducted as a simplified process, in which said methionine is obtained from a concentrated process matrix with high concentration of impurities without recrystallization. The methionine gained can be easily separated from its mother liquor and is further characterized by high purity and high bulk density. The process avoids energy consumption for dissolving and cooling in the recrystallization of the crude methionine product.

Accordingly, the present invention provides a process for the preparation of methionine in which an alkali methioninate solution is obtained by alkaline hydrolysis of 5-(2-methylmercaptoethyl)hydantoin, the process comprising the consecutive steps of (a) neutralizing the alkali methioninate solution at a temperature of between 65° C. and 95° C. by turbulent mixing with carbon dioxide in order to obtain a neutralized process solution and (b) crystallizing the methionine product in the presence of methionine seed crystals by cooling the process solution to a temperature in the range of 25° C. to 35° C.

The aforementioned high temperature in the neutralizing step (a) prevents the crude methionine product from precipitating. Uncoupling neutralization from crystallization as required according to the specific process regime and temperature profile of the present invention leads to a controlled methionine formation process. The crystallization is characterized by promoted crystal growth and reduced formation of new crystal nuclei. In this way, uncontrolled agglomeration of methionine product with inclusion of mother liquor can be prevented. In addition, the methionine product obtained by the process of the present invention can be easily separated from gas and liquid and provides high bulk densities of up to 600 g/L.

For carbonations, it is empirically found, that with increasing concentration of alkali metal hydroxide and/or alkali metal carbonate and/or alkali metal hydrogen carbonate the filtration performance worsens (see examples).

Surprisingly, the impurities present in higher concentrated crude methionine solution do not interfere with the controlled cooling crystallization in step (b) and do not lead to impure methionine product. The process according to the present invention makes it possible to conduct the process in more concentrated manner than in the conventional potassium carbonate process at which carbonation is operated at low temperature. As a side effect of more concentrated processes, an increased yield of methionine product can be obtained after crystallization, because potassium carbonates reduce the solubility of methionine in the cooled process solution.

The term "alkali methionate solution" refers to an aqueous solution of a methionine alkali metal salt. The alkali methionate solution is obtained by caustic hydrolysis of 5-(2-methylmercaptoethyl)-hydantoin ("saponification") in an alkaline process solution comprising alkali metal hydroxide and/or alkali metal carbonate and/or alkali metal hydrogencarbonate to form the methionine alkali metal salt. Preferably, the alkaline hydrolysis is carried out using potassium carbonate and potassium hydrogen carbonate to give potassium methioninate.

However, it was found that an amount of up to 30% of the potassium may be replaced by sodium, without leading to the undesired co-precipitation of sodium hydrogencarbonate in the carbonation reaction.

The potassium concentration in the hot, neutralized process solution may be between 8 wt. % and 11 wt. %, and the methionine concentration in the hot, neutralized process solution may be between 10 wt. % and 17 wt. %.

During process steps (a) and (b) the pressure may be adjusted to be between 100 kPa and 400 kPa. Preferably, the pressure may be adjusted to be between 200 kPa and 300 kPa. The pH may be adjusted to be between 7.5 and 8.5.

The pressure and the according amount of carbon dioxide added is controlled. In the neutralization step (a) the pH stays about 0.3 units above the set-point required at the crystallization step (b). During crystallization the pH is slightly decreasing and finally reaches the desired set-point.

The methionine seed crystals used in step (b) show an average particle size between 125 μm and 1000 μm, preferably having a maximum at about 250 μm.

The amount of -methionine seed crystals in the hot, neutralized process solution in step (b) may be between 5 wt. % and 15 wt. %. Preferably, the amount of methionine seed crystals in the neutralized process solution in step (b) is between 9 wt. % and 13 wt. %.

Optionally, the neutralized process solution from which the crystallization takes place additionally comprises a defoamer formulation. The defoamer suppresses foam which is formed when handling the methionine process solution or suspension. Further, the defoamer formulation contains crystallization additives to control the crystallization and facilitates three-dimensional crystal growth.

The defoamer formulation may comprise a silicone oil, preferably having a kinematic viscosity of 0.65 to 10000 $mm^2/s$ (measured at 25° C. in accordance with DIN 53018), particularly preferably from 90 to 1500 $mm^2/s$. The defoamer can further contain constituents that are effective as emulsifiers, for example ionic or non-ionic surfactants, or mixtures thereof. Suitable defoamer compositions are described e.g. in EP 1451139 B and EP 2641898 B.

The defoamer can likewise comprise silica. In a preferred embodiment, the defoamer is an aqueous solution, which comprises 5 to 10 wt. % of silicone oil, 0.05 to 1 wt. % of silica, 0.5 to 5 wt. % of a mixture of polyethoxylated fatty alcohols. The defoamer formulation may be present in an amount of between 10 ppm and 2000 ppm. Preferably, the defoamer formulation is present in an amount of between 50 ppm and 250 ppm.

The cooling period applied in step (b) is at maximum 360 min, and preferably 60 min to 180 min.

The process mixture obtained in step (b) finally is depressurized and filtered. The thus-obtained solid methionine product is washed and dried.

The process according to the invention can be carried out continuously, semi-continuously or discontinuously (batch wise). Preferably, the process is performed in continuous manner. In this case, the ratio of mass flow feed to mass flow crystallizer suspension (b) is preferably between 1:5 and 1:30. A preferred set-up for continuous operation can be found in FIG. 20.

1.) Carbonation unit for neutralization of process solution;
2.) n Crystallization units for controlled crystallization.

a-feed to neutralization
b-$CO_2$ supply
c-cooling circulation
d-feed carbonized solution to crystallizer loop
e-suspension with fine crystals
f-supersaturated mixture
g-feed of mix to the crystallizer
h-product suspension In the following, the invention is illustrated by non-limiting examples and exemplifying embodiments.

EXAMPLES

Example 1 (Comparative): Carbonation Process at 30° C.

An autoclave with agitator, fumigation, pH measurement and temperature control is equipped with potassium containing process solution with 13.5 wt. % methionine and 8.3 wt. % potassium (1200 g). Further, a silicon oil based defoamer formulation (described in EP 2641898 B) comprising ionic and non-ionic surfactants as emulsifier is added. The process solution is neutralized with carbon dioxide to pH 8 at a pressure of 3.0 bar and a temperature of 32° C. The mixture is continuously stirred with a speed of 500 rpm for evenly distributing the carbon dioxide. The resulting suspension is depressurized, filtered using vacuum (900 mbar for 10 min.+500 mbar 10 min), washed with 0° C. cold water, and finally dried. The time, necessary to collect 500 ml of filtrate is used to evaluate filtration performance. The results are summarized in Table 1.

TABLE 1

| Carbonation of methionine process solution at 30° C. | | | | | | | | | |
|---|---|---|---|---|---|---|---|---|---|
| c(Met) start [%] | c(K⁺) start [%] | Defoamer [ppm] | Time [min] | Filtration (500 ml) [s] | Yield [g] | Purity [%] | K-content [%] | Residual moisture [%] | Bulk density [g/L] |
| 13.5 | 8.3 | 50 | 22 | 322 | 133 | 76 | 7.2 | 55 | 411 |
| 13.5 | 8.3 | 250 | 21 | 118 | 120 | 82 | 5.1 | 56 | 271 |

Figure 1:
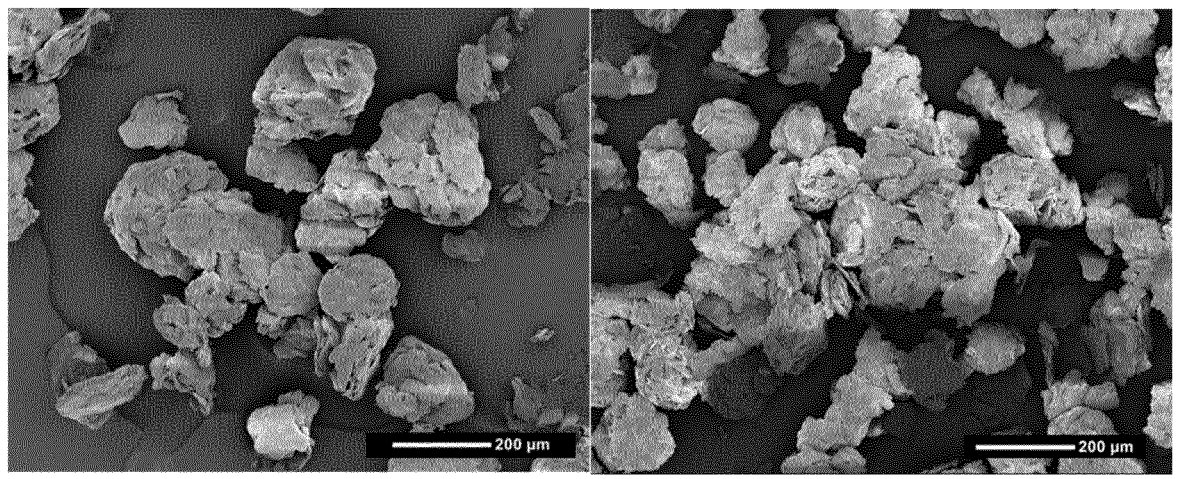
FIG. 1 shows scanning electron microscope (SEM) pictures of crude precipitated methionine as obtained by carbonation at 30° C.: low concentration of defoamer (left) and high concentration of defoamer (right), see Example 1.
Figure 2:
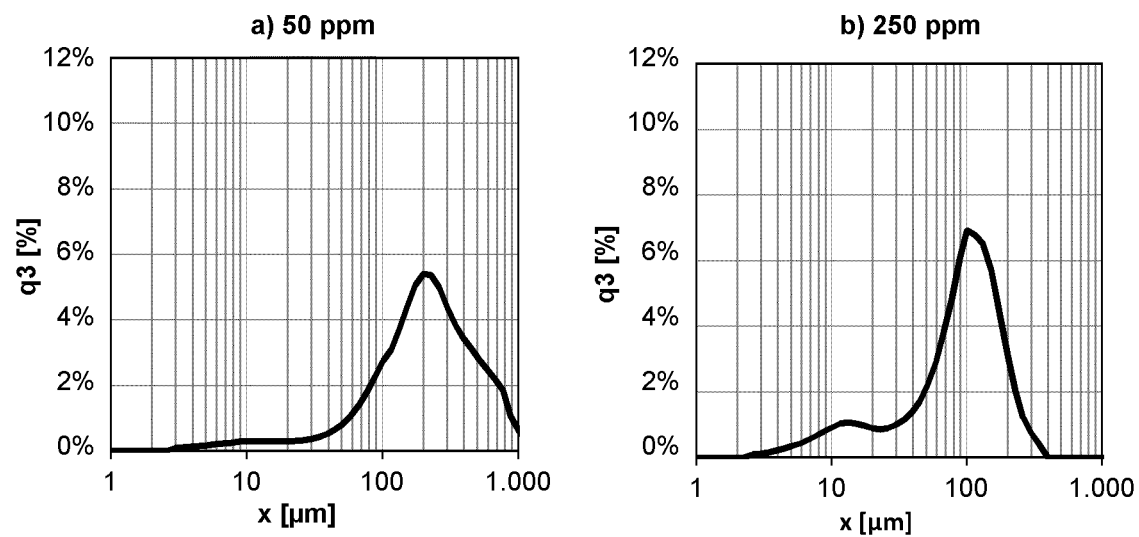
FIG. 2 shows the corresponding particle size distribution ($q_3$) diagram (PSD), measurement after 120 s ultrasound for Example 1.

In above-described carbonation at 30° C. raw methionine is precipitated, which contains impurities from incorporated mother liquor and high residual moisture (crystals are shown in FIG. 1). The solid-liquid separation shows low performance. Increasing concentration of defoamer is improving the filtration performance. The formed particles are agglomerated and can be easily destroyed by ultrasound (PSD, Horiba LA-950 V Fa. Retsch, FIG. 2). Due to the low purity of the obtained product, the bulk density is a non-relevant parameter.

Example 2 (Comparative): Carbonation at Elevated Temperature and Subsequent Crystallization without Seed Material An autoclave with agitator, fumigation, pH measurement and temperature control is equipped with potassium containing process solution with 13.5 wt. % methionine and 8.7 wt. % potassium (1200 g).

Further, 500 ppm of a silicon oil based defoamer formulation (described in EP 2641898 B) comprising ionic and non-ionic surfactants as emulsifier is added. The process solution is neutralized to pH 8 with carbon dioxide at a pressure of 1.0-3.0 bar. Temperature is kept above 80° C.

Figure 3:
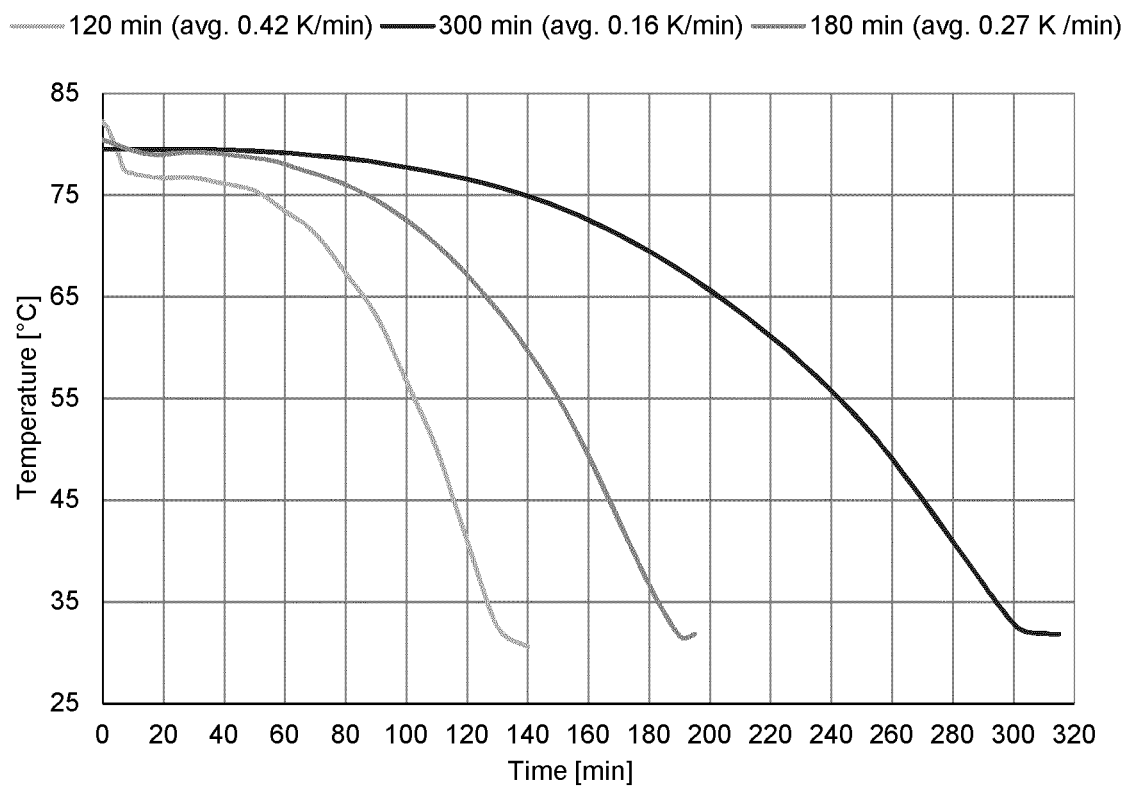
FIG. 3 shows typical cubic cooling profile for 120 min, 180 min and 300 min.

A controlled cooling program from 80 to 32° C. is applied for controlled crystallization during continuous stirring at a speed of 250 rpm. The typical shape of the cubic cooling profile for 180 min and 300 min is shown in FIG. 3.

The thus-obtained suspension is depressurized, filtered using vacuum (900 mbar for 10 min. & 500 mbar 10 min), washed with 0° C. cold water, and finally dried. The time, necessary to collect 500 ml of filtrate is used to evaluate filtration performance. The results are summarized in Table 2.

TABLE 2

Carbonation and crystallization of methionine raw solution without seeding

| c(Met) start [%] | c(K⁺) start [%] | Defoamer [ppm] | Time (cooling) [min] | Filtration (500 ml) [s] | Yield [g] | Purity [%] | Residual moisture [%] | Bulk density [g/L] |
|---|---|---|---|---|---|---|---|---|
| 13.5 | 8.7 | 500 | 180 | 409 | 96 | 99.6 | 31 | 248 |

Figure 6:
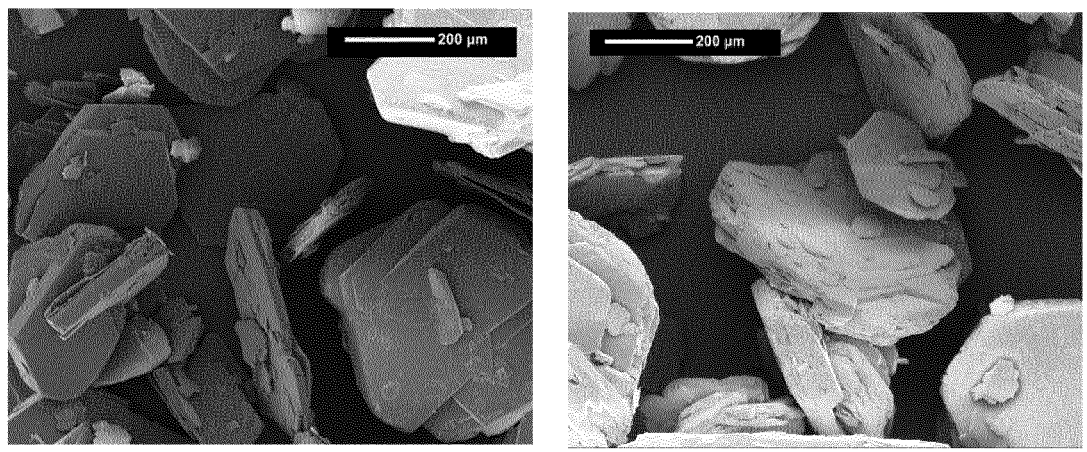
FIG. 6 shows SEM picture of the seed material (left) and crystalline product of Example 3 (right).

The filtration of the obtained methionine suspension is difficult. The particles are comparable to those flat leaflet type crystals gained by carbonation at 30° C. (Example 1). But the obtained product has a higher purity, as there is less mother liquor is incorporated. The filter cake retains only 31% residual moisture. After drying, the bulk density is very low. This can be explained by the morphology (flat, fine particles with rough surfaces; SEM pictures (FIG. 4) and many fine crystals below 100 μm. Particles sizes (compare PSD, FIG. 6) are similar to material gained by carbonation at 30° C. (Example 1).

Example 3: Carbonation at Elevated Temperature and Subsequent Crystallization with Seed Material General Procedure An autoclave with agitator, fumigation, pH measurement and temperature control is equipped with 1200 g potassium containing process solution with a defined concentration of methionine in the range of 12.0-17.0 wt. % and potassium in the range of 7.0-12.0 wt. %.

Further 0-800 ppm of a silicon oil based defoamer formulation containing mixtures of ionic and non-ionic surfactants as emulsifier (described in EP 2641898 B) is added. The solution is neutralized to pH 8 with carbon dioxide at a pressure of 1.0-3.0 bar and a temperature in the range of 65 to 95° C. depending on the concentration to prevent precipitation.

Figure 7:
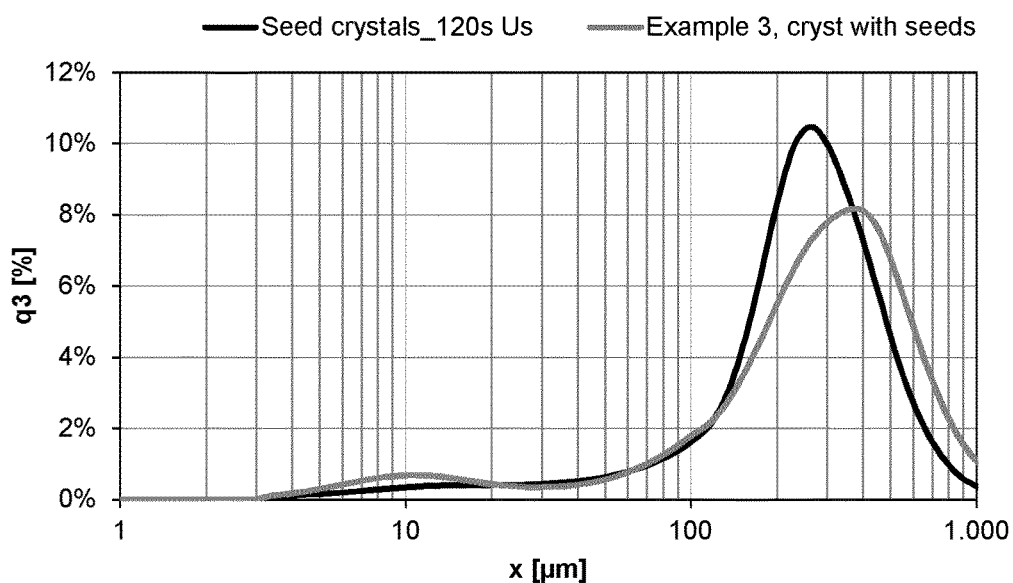
FIG. 7 shows a PSD diagram for Example 3 including the seed material.

About 5° C. above nucleation temperature, seed crystals (0 g-100 g) are added in one batch. The seed crystals used, consist of two fractions in mass ratio from 1.6:1 to 1.2:1 (250 μm to 1000 μm:125 to 250 μm). The seed crystals are prepared from a matrix in which crystallization additives according to EP 2641898 B are present and separated by sieving to fractions. The particle size distribution (PSD) of the seeds (all fractions) is shown in FIG. 7. The maximum is located at approx. 250 μm.

During continuous stirring at a speed of 100 and 500 rpm a cubic temperature controlled cooling program to 32° C. controls crystallization (compare FIG. 3). The obtained suspension is depressurized, filtered using vacuum (900 mbar for 10 min & 500 mbar 10 min), washed with 0° C. cold water, and finally dried. The time, necessary to collect 500 ml of filtrate is used to evaluate filtration performance.

For all PSD, ultrasound (120 s) is applied before starting the measurement (PSD, Horiba LA-950 V Fa. Retsch).

Example 3a

An autoclave with agitator, fumigation, pH measurement and temperature control is equipped with potassium containing process solution with 13.1 wt. % methionine and 8.0 wt. % potassium (1200 g).

Further, 600 ppm of a silicon oil based defoamer formulation (EP 2641898 B) is added. The process solution is neutralized to pH 8 with carbon dioxide at a pressure of 2.0-3.0 bar and at a temperature of 85° C.

At 83° C. seed crystals (60 g) are added. During continuous stirring at a speed of 250 rpm a temperature controlled cooling program to 32° C. is applied (cubic profile within 180 min, avg. 0.28 K/min, compare FIG. 3). The thus-obtained suspension is depressurized, filtered using vacuum (900 mbar for 10 min & 500 mbar 10 min), washed with 0° C. cold water, and finally dried. The time, necessary to collect 500 ml of filtrate is used to evaluate filtration performance. The results are summarized in Table 3.

TABLE 3

Crystallization with seeds, 600 ppm defoamer and 80 g/kg potassium

| c(Met) start [%] | c(K⁺) start [%] | Seed crystals/ ratio [g] | Defoamer [ppm] | Time (cooling) [min] | Filtration (500 ml) [s] | Yield [g] | Purity [%] | Residual moisture [%] | Bulk density [g/L] |
|---|---|---|---|---|---|---|---|---|---|
| 13.1 | 8.0 | 160 g/1.4:1 | 600 | 190 | 87 | 139 | 100 | 13 | 601 |

The quality of the obtained D,L-methionine is excellent with respect to purity and bulk density. The filtration properties of the thus-obtained particles are improved versus those gained by reference carbonation at 30° C. (Example 1). The filter cake retains 12.5% residual moisture after a fast filtration time. The particle size distribution (bimodal profile) shows formation of new crystals gained by nucleation and growth of the seeds to bigger particles, compared to the seed material (FIG. 7)

Example 4: Carbonation at Elevated Temperature and Subsequent Crystallization with Seed Material (Repeatability)

In order to evaluate the repeatability of the results with the chosen setup, the experiment is repeated three times in accordance with the general procedure indicated in Example 3.

An autoclave with agitator, fumigation, pH measurement and temperature control is equipped with 1200 g potassium containing process solution with a defined concentration of methionine of 13.5 wt. %. Further, 250 ppm of a silicon oil based defoamer formulation (described in EP 2641898 B) is added. The process solution is neutralized to pH 8 with carbon dioxide at a pressure of <3.0 bar and the temperature is kept above 80° C.

At 85° C., seed crystals (60 g, 1.4:1; see general procedure Example 3) are added and under continuous stirring a temperature controlled cooling program is applied (from 80 to 32° C. in cubic profile within 210 min, avg. 0.25 K/min). The thus-obtained suspension is depressurized, filtered using vacuum (900 mbar for 10 min & 500 mbar 10 min), washed with 0° C. cold water, and finally dried.

TABLE 4

Repeatability of crystallization with seeding, 250 ppm defoamer.

| c(Met) start [%] | c(K$^+$) start [%] | Seed crystals/ratio | Defoamer [ppm] | Time (cooling) [min] | Filtration (500 ml) [s] | Yield [g] | Purity [%] | Residual moisture [%] | Bulk density [g/L] |
|---|---|---|---|---|---|---|---|---|---|
| 13.5 | 8.3 | 60 g/1.4:1 | 250 | 210 | 25 | 167 | 99.1 | 15 | 539 |
| 13.5 | 8.7 | 60 g/1.4:1 | 250 | 210 | 23 | 165 | 100 | 13 | 552 |
| 13.5 | 8.3 | 60 g/1.4:1 | 250 | 210 | 15 | 165 | 100 | 13 | 547 |

Figure 8:
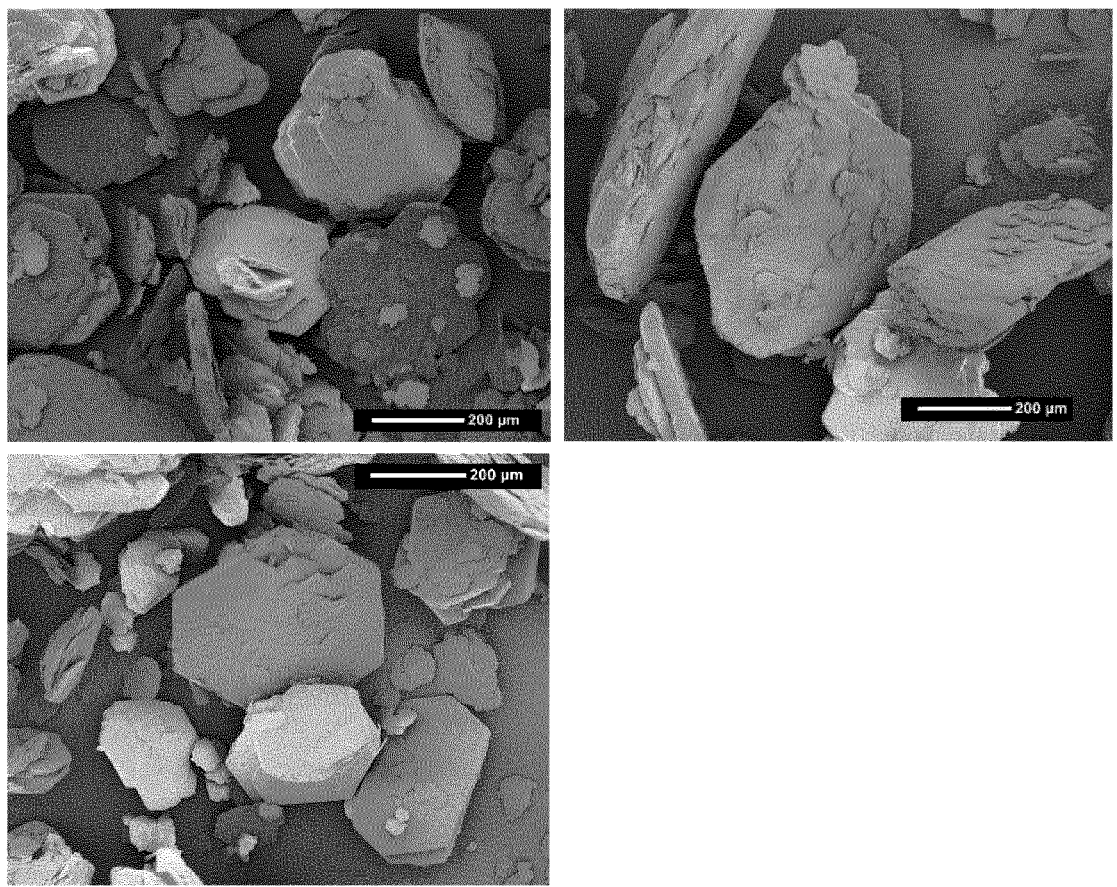
FIG. 8 shows three SEM pictures of Example 4 to proof the repeatability of the process.
Figure 9:
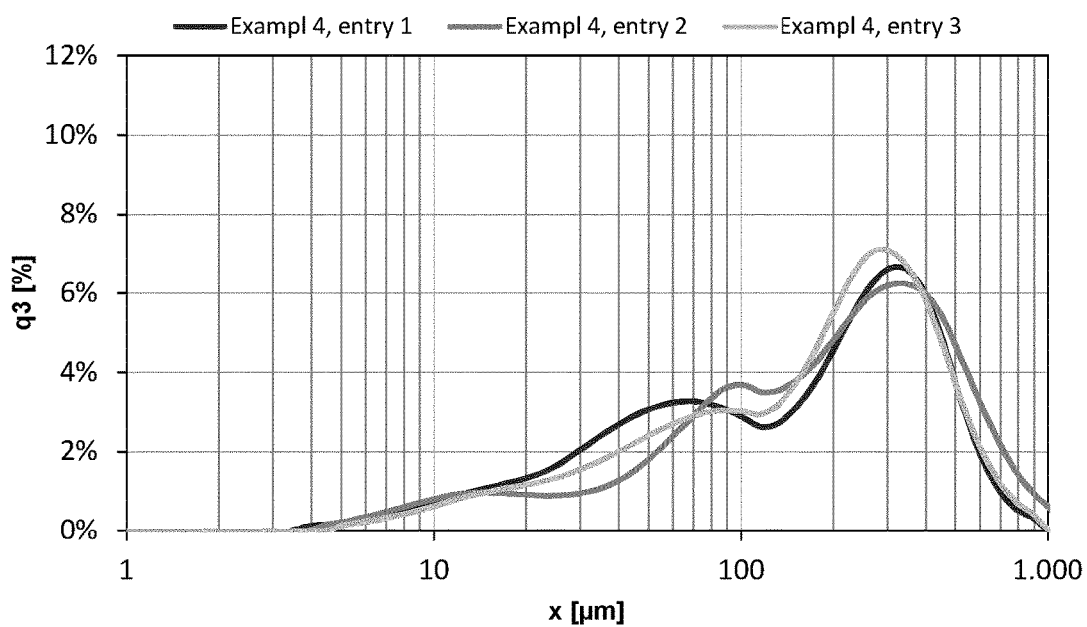
FIG. 9 shows the PSD of Example 4. All entries show a similar pattern, but some deviations observed.

The repeatability of the process setup is proven by repetition of the experiment under the same conditions. It is possible to control the process and to obtain crystalline product in desired quality. The material obtained from three experiments shows very similar PSD, SEM and bulk density (FIGS. 8 & 9). The filter cake retains 13%-15% residual moisture and is easy to wash and handle.

Example 5: Influence of Defoamer and Crystallization Additives

Process solution: 13.5 wt. % methionine and 8.7 wt. % or 8.3 wt. % potassium. Procedure according to general procedure (Example 3).

Different amounts of defoamer are used in order to investigate their influence on the crystallization process. A cubic cooling profile is applied (cooling from 80 to 32° C. in cubic profile within 180 min, avg. 0.28 K/min, FIG. 3) and the mass of seed crystals is kept constant (60 g).

TABLE 5

Influence of defoamer on the crystallization.

| c(Met) start [%] | c(K$^+$) start [%] | Seed crystals/ratio [g] | Defoamer [ppm] | Time (cooling) [min] | Filtration (500 ml) [s] | Yield [g] | Purity [%] | Residual moisture [%] | Bulk density [g/L] |
|---|---|---|---|---|---|---|---|---|---|
| 13.5 | 8.3 | 60 g/1.4:1 | — | 180 | 14 | 165.5 | 99.9 | 18 | 497 |
| 13.5 | 8.7 | 60 g/1.4:1 | 50 | 180 | ~8 | 159.5 | 99.8 | 15 | 520 |
| 13.5 | 8.3 | 60 g/1.4:1 | 250 | 180 | 23 | 165.3 | 100 | 14 | 537 |
| 13.5 | 8.7 | 60 g/1.4:1 | 500 | 180 | 26 | 167.9 | 100.5 | 15 | 539 |

Figure 10:
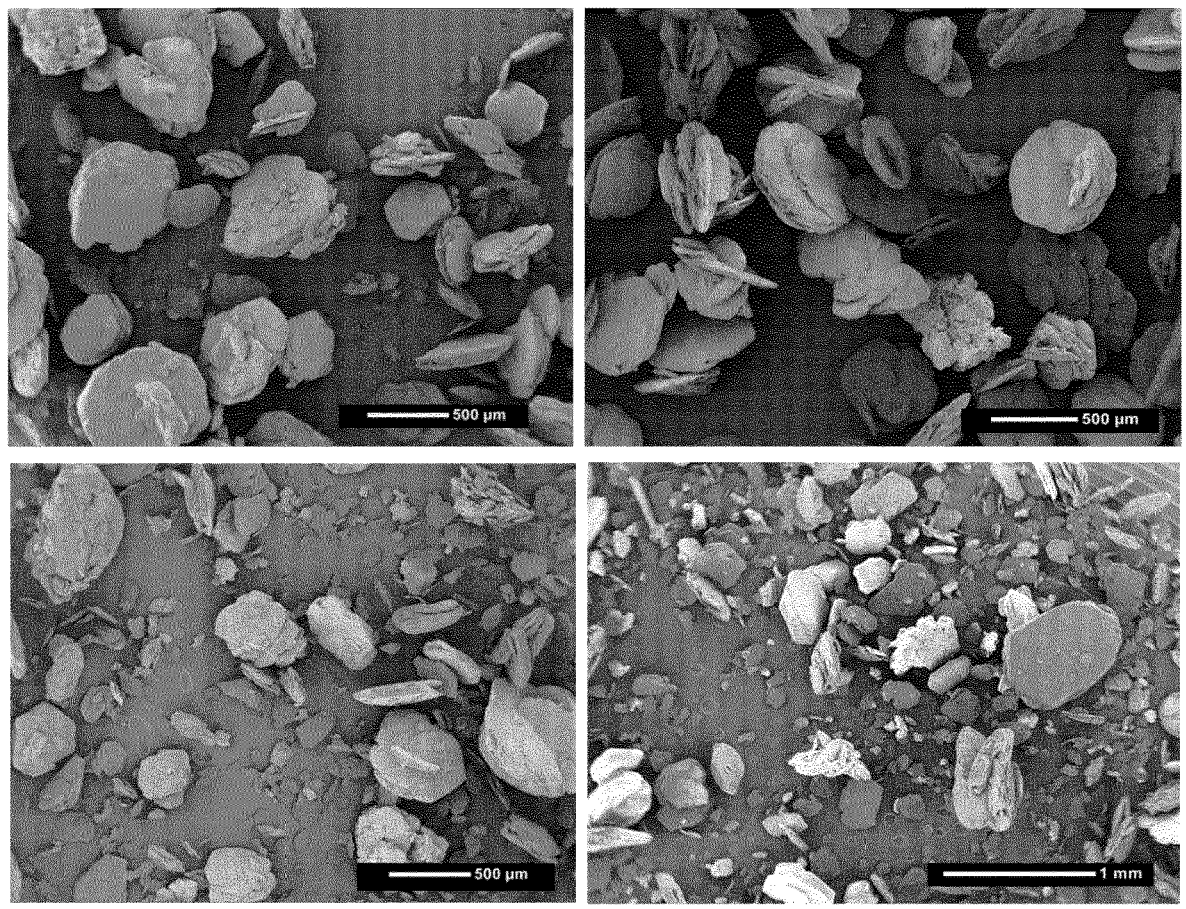
FIG. 10 shows SEM pictures of Example 5 (top left=entry 1; top right=entry 2, bottom left=entry 3; bottom right=entry 4).
Figure 11:
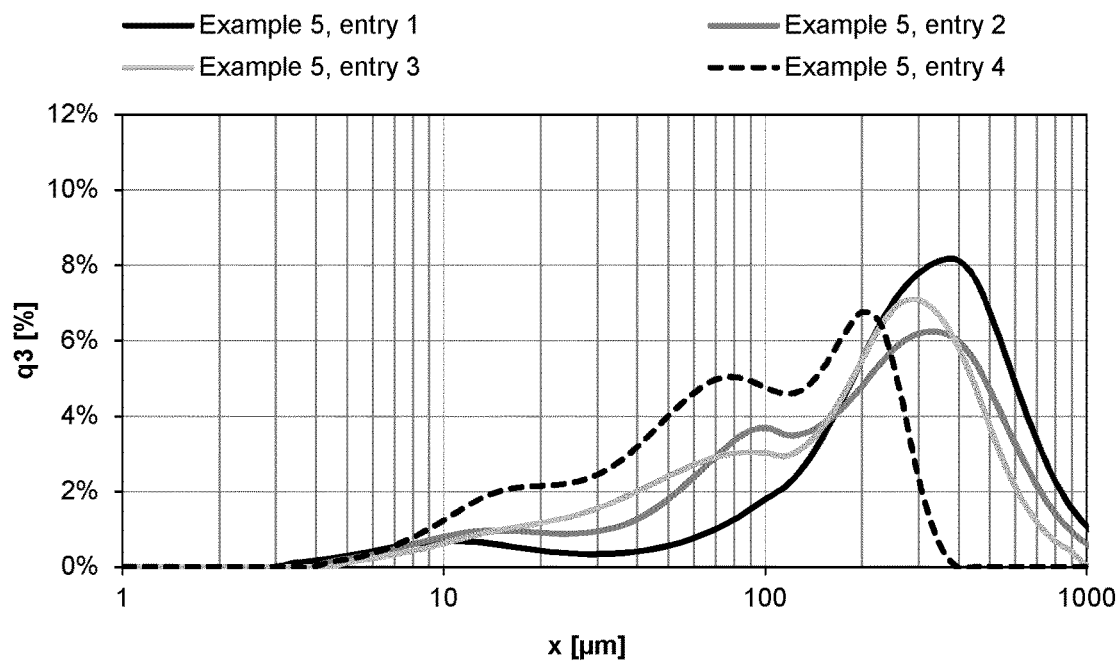
FIG. 11 depicts the influence of crystallization additives on PSD, in accordance with Example 5.

With increasing concentration of the defoamer present in the solution, the bulk density also slightly increases. Above 250 ppm defoamer no significant effect with respect to bulk density is observed. Entries 1-4 in table 5 and the corresponding FIG. 10 show that the additive amount has significant influence on the particle size distribution (PSD). The additives slow down the crystal growth and the nucleation process is accelerated. The formation of smaller particles increases the bulk density from 497 to 539 g/L. With respect to filtration performance, the optimum is found between 50 ppm and 250 ppm defoamer.

Example 6: Influence of Cooling Profile

Process solution: 13.5 wt. % methionine and 8.7 wt. % potassium. Procedure according to general procedure (Example 3).

Figure 4:
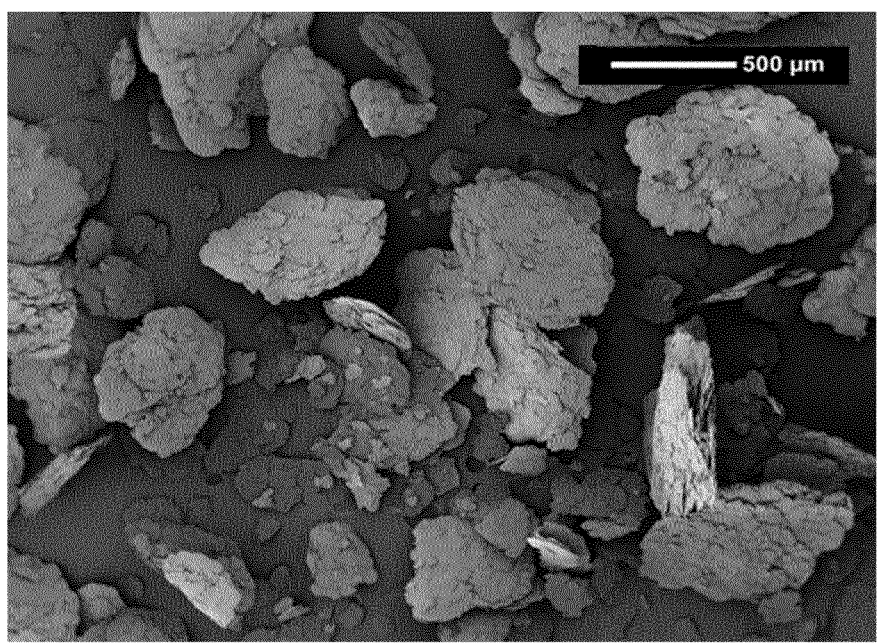
FIG. 4 shows SEM picture of D,L-methionine as obtained by carbonation at elevated temperature and subsequent crystallization without seed material, see Example 2.
Figure 5:
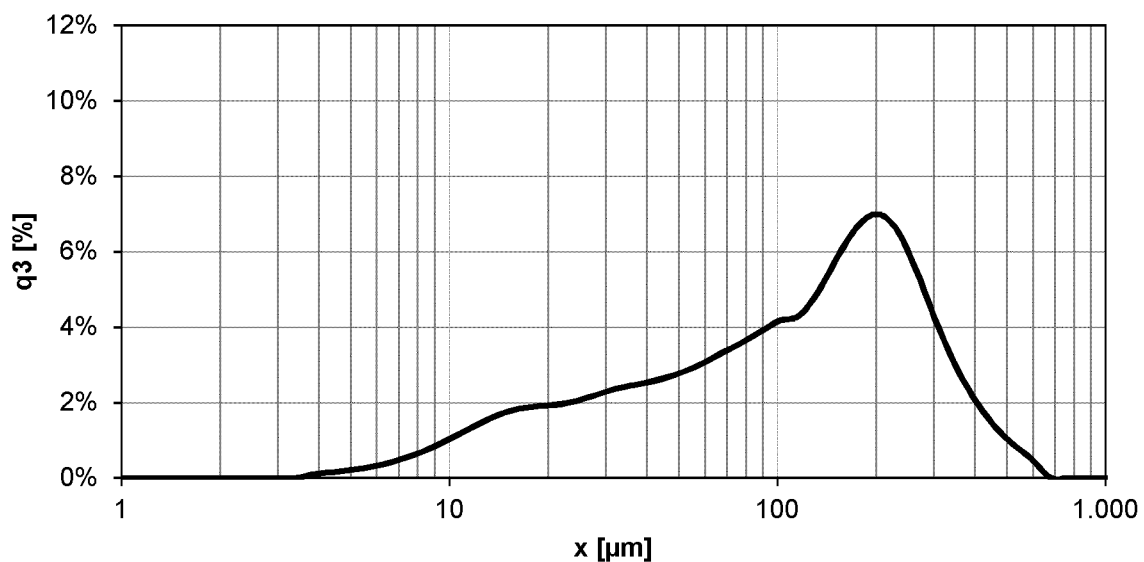
FIG. 5 shows the corresponding PSD diagram of Example 2—crystallization without seeding.

In order to determine the influence of the cooling profile, two cubic profiles are tested with duration of 120 min (avg. 0.47 K/min) or 300 min (avg. 0.16 K/min); compare FIG. 4.

The amount of seed crystals is kept constant (60 g), but the ratio of seed fractions is varied from 1.2:1 to 1.6:1 (for particular particle size of fractions see general procedure in Example 3).

TABLE 6

Influence of cooling profile on the crystallization.

| c(Met) start [%] | c(K⁺) start [%] | Seed crystals/ ratio [g] | Defoamer [ppm] | Time (cooling) [min] | T (start) [° C.] | Filtration (500 ml) [s] | Yield [g] | Purity [%] | Residual moisture [%] | Bulk density [g/L] |
|---|---|---|---|---|---|---|---|---|---|---|
| 13.5 | 8.3 | 60 g/1.6:1 | 250 | 120 | 79.5 | 31 | 167 | 99.7 | 16 | 520 |
| 13.5 | 8.7 | 60 g/1.6:1 | 250 | 300 | 79.5 | 20 | 166 | 100 | 12 | 561 |
| 13.5 | 8.3 | 60 g/1.2:1 | 250 | 120 | 79.5 | 30 | 167 | 99.9 | 15 | 532 |
| 13.5 | 8.7 | 60 g/1.2:1 | 250 | 300 | 79.5 | 17 | 166 | 100 | 13 | 554 |

Figure 12:
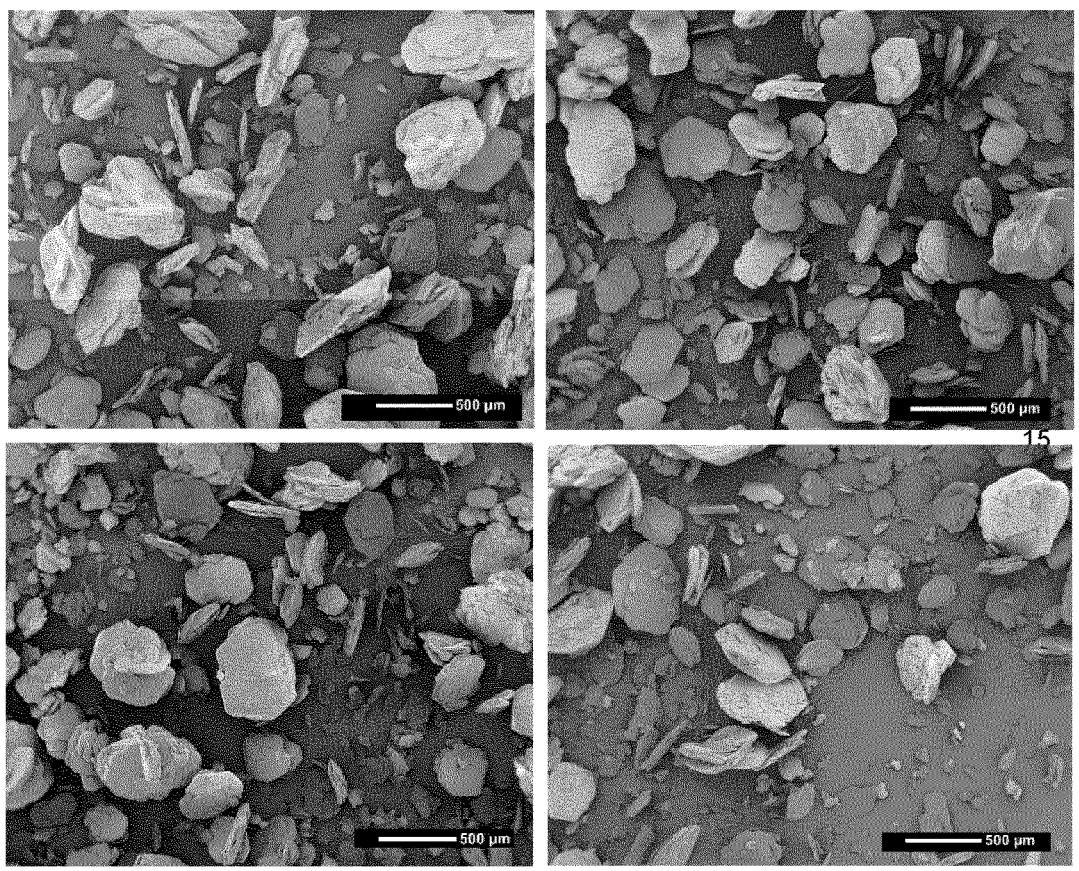
FIG. 12 shows SEM pictures from crystalline D,L-methionine from Example 6, gained by different cooling profiles/seed crystal ratios.
Figure 13:
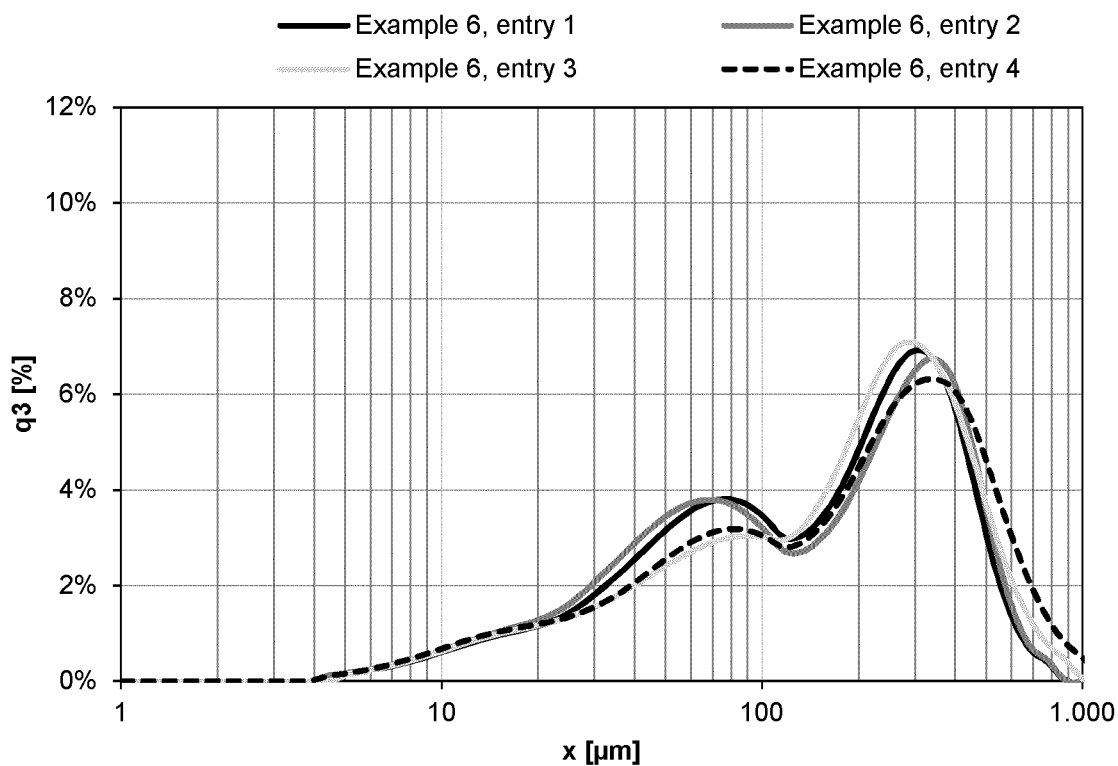
FIG. 13 shows the PSD of the methionine product from Example 6.

An elongated cooling profile improves quality of the obtained methionine crystals. More residence time allows slower crystallization. Supersaturation is reduced by growth on seed crystals and nucleation is suppressed. PSD and SEM prove higher quality of the slow gained material. The bulk density increases from 520 to 560 g/L if the 300 min cooling profile is applied. Reduced time for crystallization increases formation of fine crystals via nucleation. The particle size of the seed crystals have no or only limited effect with respect to the final bulk density or PSD (see FIGS. 12 & 13).

Example 7: Influence of Seeding Crystal Amount

Process solution: 13.5 wt. % methionine and 8.7 wt. % potassium. Procedure according to general procedure (Example 3). A cubic cooling profile with 180 min (avg. 0.27 K/min; see FIG. 3) is applied.

In order to investigate the influence of the total crystal surface area available for crystal growth, the mass of seed crystals is varied (40 g seed crystals and 80 g seed crystals, ratio of seed fractions 1.4:1).

TABLE 7

Influence of amount of seed crystals on the crystallization.

| c(Met) start [%] | c(K⁺) start [%] | Seed crystals/ ratio | Defoamer [ppm] | Time (cooling) [min] | T (start) [° C.] | Filtration (500 ml) [s] | Yield [g] | Purity [%] | Residual moisture [%] | Bulk density [g/L] |
|---|---|---|---|---|---|---|---|---|---|---|
| 13.5 | 8.3 | 40 g/ 1.4:1 | 200 | 180 | 79.4 | 32 | 167 | 99.7 | 18 | 476 |
| 13.5 | 8.7 | 80 g/ 1.4:1 | 200 | 180 | 79.6 | 17 | 166 | 100 | 12 | 555 |

Figure 14:
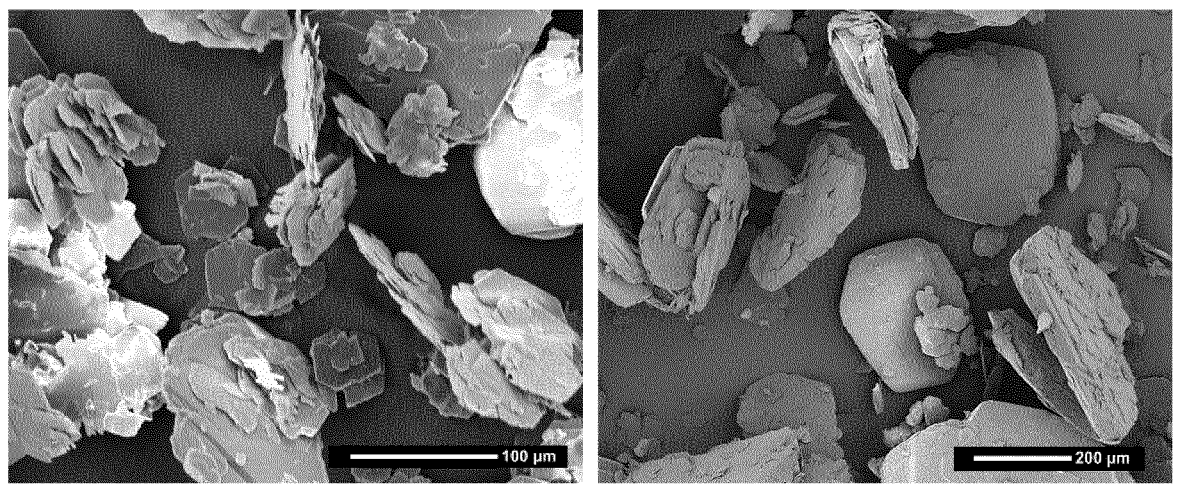
FIG. 14 shows SEM pictures from crystalline D,L-methionine from Example 7.
Figure 15:
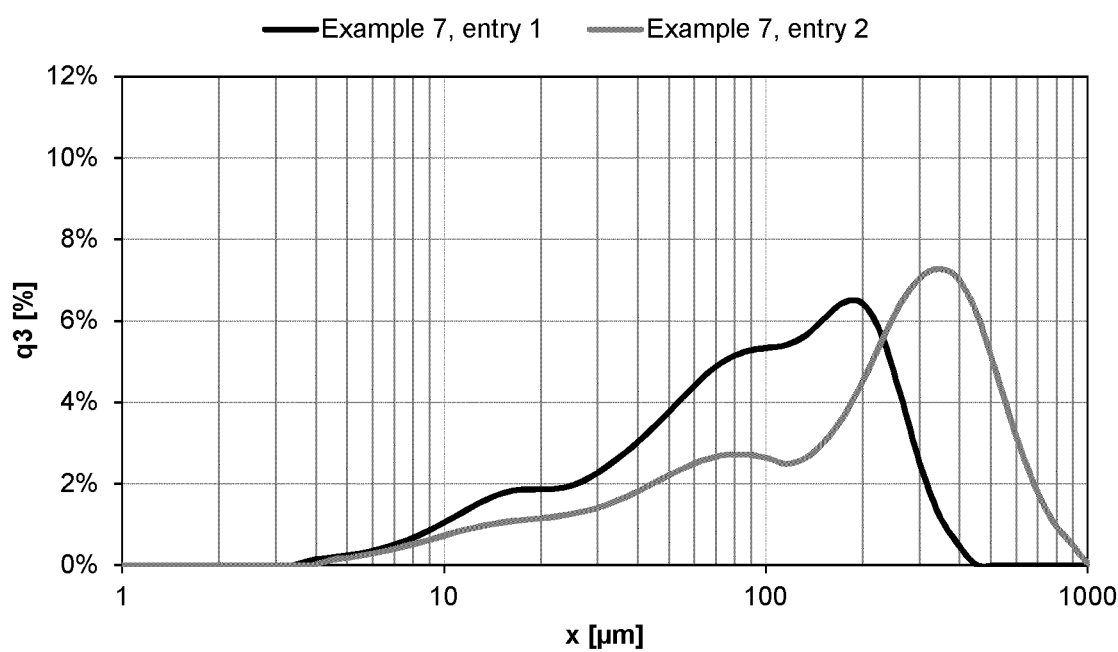
FIG. 15 shows the PSD of the methionine product from Example 7. Too low amount of seeding crystals (entry 1) results in formation of more nuclei instead of crystal growth.

With increasing mass of seed crystals (surface area), the bulk density and average particle size increases. Entry 2 in Table 7 shows improved crystal quality with less rough surfaces (FIGS. 14 & 15). The chosen parameters allow controlled crystallization, promoting crystal growth and suppressing nucleation. With respect to filtration performance the cake resulting from the second entry has improved filtration properties, less fines and lower residual moisture.

Example 8: Higher Concentrated Process Solution

Process solution: 15.1 wt. % methionine and 9.3 wt. % potassium. Procedure according to general procedure (Example 3). A cubic cooling profile with 180 min is applied and the mass of seed crystals varies from 60 g to 80 g to change the total crystal surface area available for crystal growth (ratio of seed fractions 1.4:1).

TABLE 8

Influence of seeding amount on higher concentration crystallization

| c(Met) start [%] | c(K+) start [%] | Seed crystals/ ratio [g] | Defoamer [ppm] | Time (cooling) [min] | T (start) [° C.] | Filtration (500 ml) [s] | Yield [g] | Purity [%] | Residual moisture [%] | Bulk density [g/L] |
|---|---|---|---|---|---|---|---|---|---|---|
| 15.1 | 9.3 | 60 g/ 1.4:1 | 250 | 180 | 79.5 | 55 | 196 | 100 | 11 | 490 |
| 15.1 | 9.3 | 80 g/ 1.4:1 | 250 | 180 | 79.8 | 16 | 198 | 100 | 6 | 552 |

Figure 16:
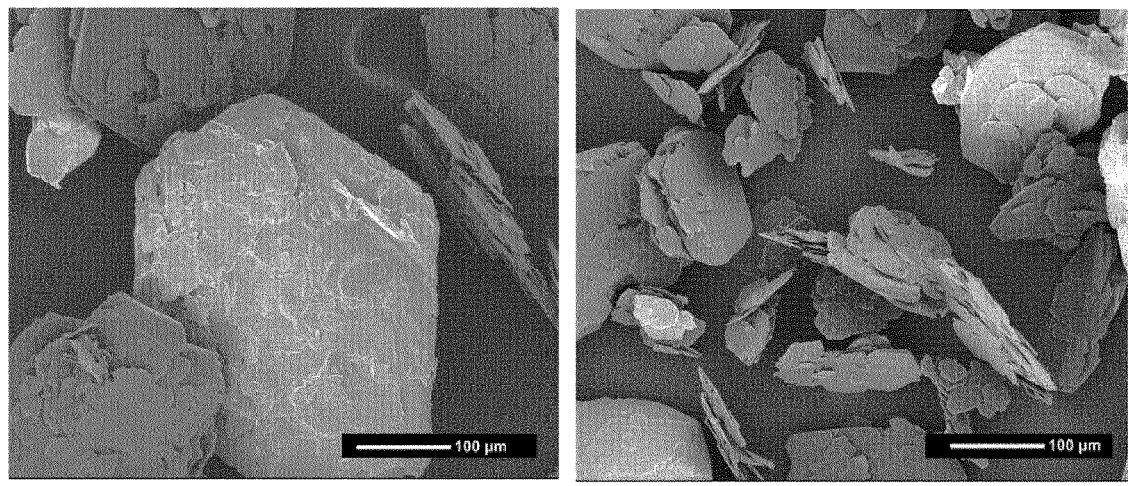
FIG. 16 shows SEM pictures from crystalline D,L-methionine from Example 8.
Figure 17:
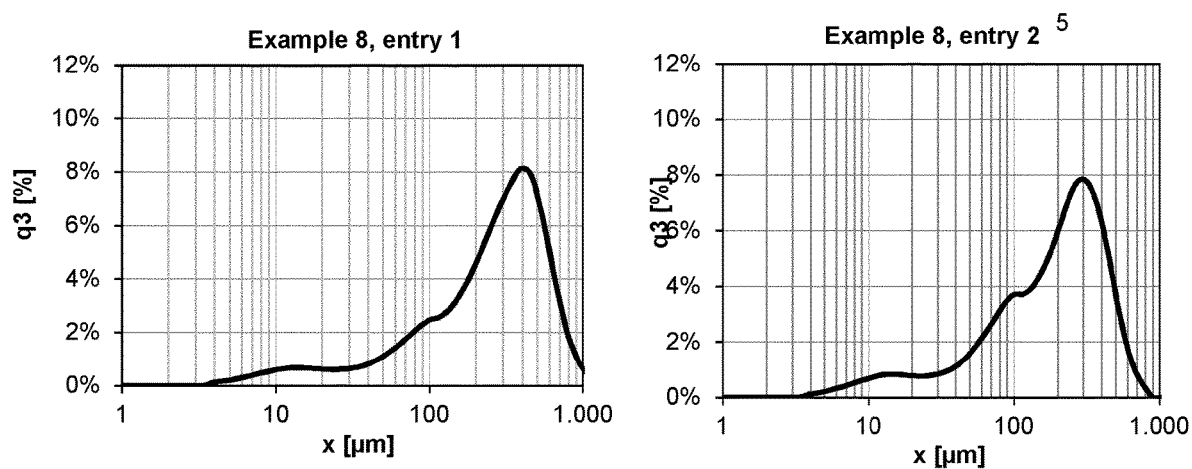
FIG. 17 shows the PSD of the methionine crystals from Example 8 using high (left) and low (right) amounts of seed crystals.

With higher concentration of methionine and other process parameters maintaining constant, the supersaturation increases. Therefore, the total crystal surface area of the seed crystals is important for controlling the crystal growth. Entry 2 shows higher bulk density and higher average particle size (FIGS. 16 & 17). The chosen parameters still allow controlled crystallization with crystal growth and suppressed nucleation. With respect to filtration performance, the cake resulting from the second entry has improved filtration properties, less fines and very low residual moisture.

Example 9: Continuous Process

Figure 20:
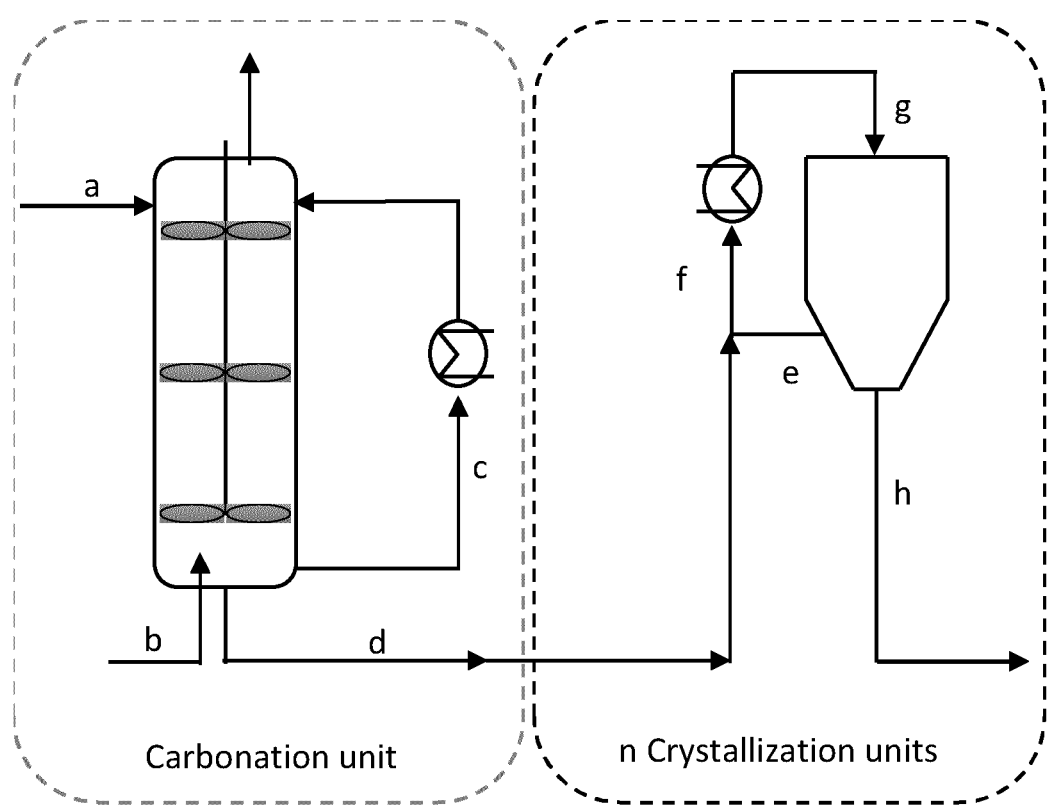
FIG. 20 provides a general overview of continuous process and its units.

FIG. 20 shows the set up for the continuous process. It requires several process units. In a first process unit, the process solution is neutralized. The second process unit consists of at least one crystallizer. Each crystallizer is operated at constant temperature. Depending on the number (n) of crystallization vessels, the cooling occurs in n-steps, approximating a cooling profile.

Following example describes a set up with one crystallization stage:

A vessel with agitator, fumigation, pH measurement and temperature control is continuously fed with a potassium containing process solution [(a), 12.0-17.0 wt. % methionine 7.0-12.0 wt. % potassium and 250 ppm of a silicon oil based defoamer formulation according EP 2641898 B included)]. The process solution is continuously neutralized to pH 8.0 with carbon dioxide (b) at a pressure of 2.0-3.0 bar and at a temperature of 85° C. (c) under continuous stirring. The neutralized solution is transferred via heat traced piping into the crystallization unit (d) and mixed with the suspension (e).

For the start up, the crystallizer is equipped with a methionine suspension (15 wt. % solids). These solids act as seed crystals during start up. As for the batch process, the solids consist of two fractions in mass ratio from 1.6:1 to 1.2:1 (250 µm to 1000 µm:125 to 250 µm)). During continuous operation, the crystallizer is operated constantly at 32° C. using an external heat exchanger. The crystallizer is kept under the same pressure as the neutralization unit. The mass flow ratio of carbonized feed solution to circulating crystallizer suspension is adjusted to a value in the range between 1:5 and 1:20.

The thus-obtained suspension (h) is collected, depressurized, filtered using vacuum (900 mbar for 10 min & 500 mbar 10 min), washed with 0° C. cold water, and finally dried.

After continuous operation for 24 h (13.5 wt. % methionine 8.3 wt. % potassium and 250 ppm of a silicon oil based defoamer formulation according EP 2641898 B) a sample of 1 L product is collected, depressurized, filtered, washed with 0° C. cold water, and finally dried (Table 9).

TABLE 9

| | | | | Continuous operation | | | | |
|---|---|---|---|---|---|---|---|---|
| c(Met) start [%] | c(K+) start [%] | Feed ratio | Defoamer [ppm] | Filtration (500 ml) [s] | Yield [g] | Purity [%] | Residual moisture [%] | Bulk density [g/L] |
| 13.5 | 8.5 | 1:10 | 250 ppm | 20 | 120.6 | 99.9 | 12 | 565 |

Figure 18:
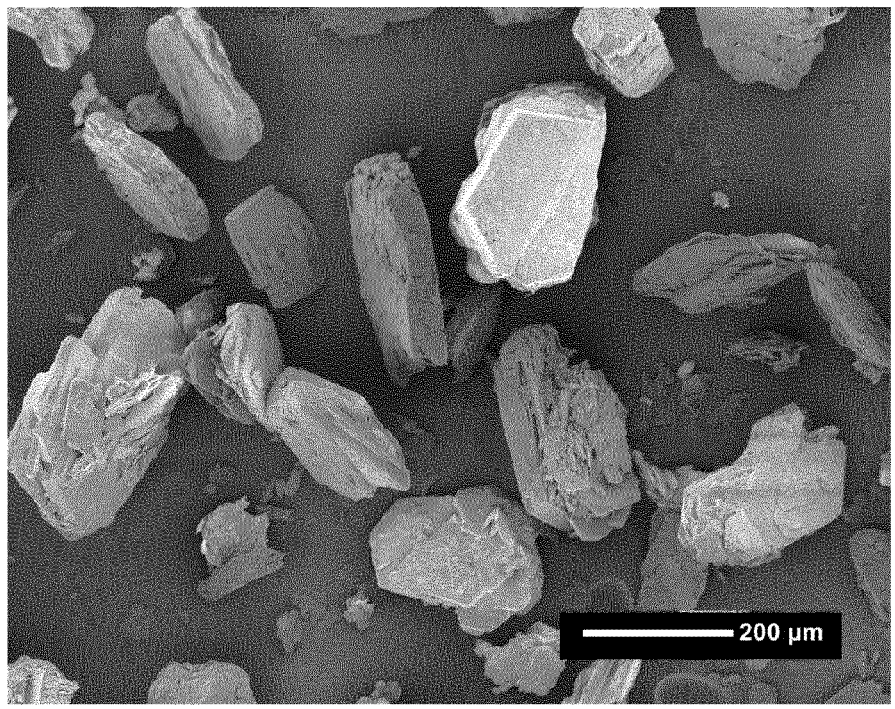
FIG. 18 shows SEM pictures from crystalline D,L-methionine from Example 9.
Figure 19:
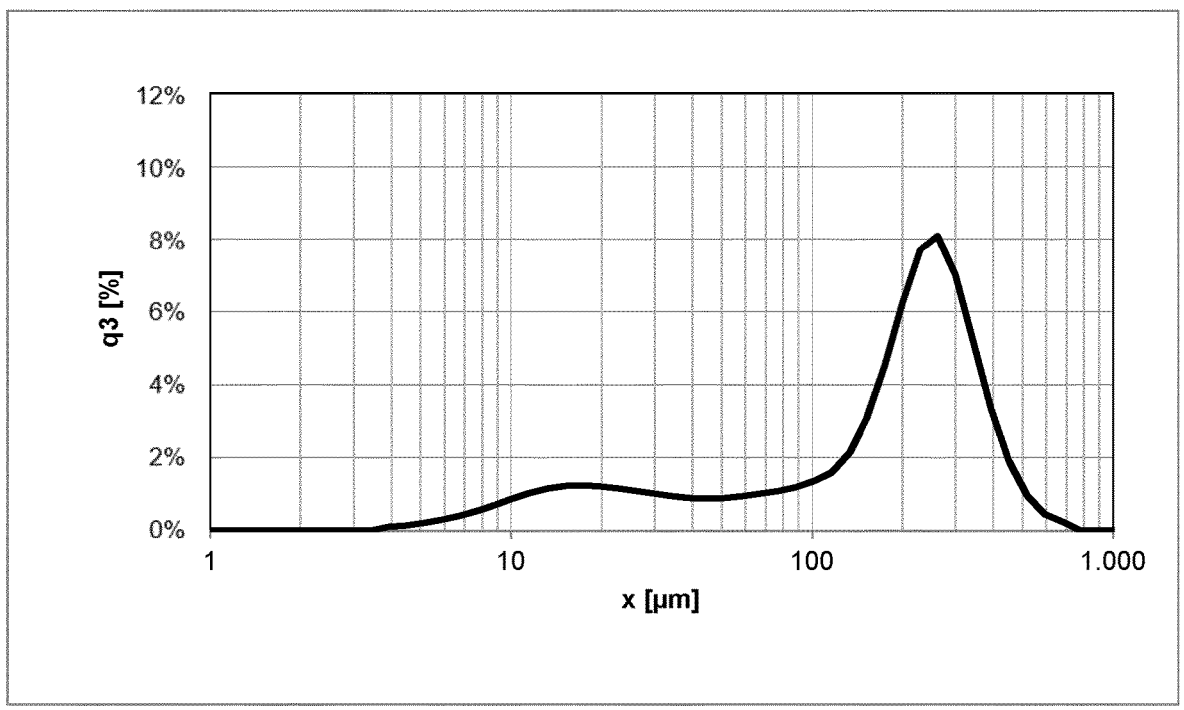
FIG. 19 shows the PSD of the methionine crystals from continuous operation of Example 9.

The quality of the obtained D,L-methionine is excellent with respect to purity and bulk density. The filter cake retains 12% residual moisture after a fast filtration time. The particle size distribution shows formation of new crystals gained by nucleation and growth of the seeds to bigger particles, compared to the seed material (FIGS. 18 & 19)

The invention claimed is:
1. A process for preparing D,L-methionine wherein an alkali methioninate solution is obtained by alkaline hydrolysis of 5-(2-methylmercaptoethyl)-hydantoin, the process comprising:

(a) neutralizing the alkali methioninate solution at a temperature of 65° C. and 95° C. by turbulent mixing with carbon dioxide in order to obtain a neutralized process solution; and (b) crystallizing D,L-methionine in the presence of a D,L-methionine seed crystal by cooling the neutralized process solution to a temperature of 25° C. to 35° C.

2. The process of claim 1, wherein the alkali methioninate has a formula $(K_{1-x}Na_x)^+(C_5H_{10}NO_2S)^-$, wherein $0 \leq x \leq 0.3$.

3. The process of claim 2, wherein potassium is present in the neutralized process solution in an amount of 8 wt. % to 11 wt. %, based on a total weight of neutralized process solution.

4. The process of claim 1, wherein methionine is present in the neutralized process solution in an amount of 10 wt. % and 17 wt. %, based on a total weight of neutralized process solution.

5. The process of claim 1, wherein during (a) and (b) the pressure is adjusted to be 100 kPa to 400 kPa and the pH is adjusted to be 7.5 to 8.5.

6. The process of claim 1, wherein the D,L-methionine seed crystal has an average particle size of 125 μm to 1000 μm.

7. The process of claim 1, wherein the D,L-methionine seed crystal is present in the neutralized process solution in an amount of 5 wt. % to 15 wt. %, based on a total weight of neutralized process solution.

8. The process of claim 1, wherein the neutralized process solution further comprises a defoamer formulation.

9. The process of claim 8, wherein the defoamer formulation is present in an amount of 10 ppm to 2000 ppm.

10. The process of claim 8, wherein the defoamer formulation comprises a silicone oil having a kinematic viscosity of 0.65 to 10000 mm$^2$/s measured at 25° C. in accordance with DIN 53018.

11. The process of claim 8, wherein the defoamer formulation comprises an emulsifier comprising at least one selected from the group consisting of ionic surfactants and non-ionic surfactants.

12. The process of claim 1, wherein the cooling is performed for 0.01 to 360 min.

13. The process of claim 1, wherein the process is a batch process.

14. The process of claim 1, wherein the process is a continuous process.

* * * * *